United States Patent [19]
Bower et al.

[11] Patent Number: 5,126,328
[45] Date of Patent: Jun. 30, 1992

[54] PROCESS FOR CROSSLINKING GELATIN

[76] Inventors: David K. Bower, 2327 St. Ignace, Wyandotte, Mich. 48192; Frederick K. Chaundy, 28731 S. Point Dr., Grosse Ile, Mich. 48138; Terence K. Kilbride, Jr., 5501 Lakeview Dr., Bloomfield Hills, Mich. 48302

[21] Appl. No.: 639,468

[22] Filed: Jan. 10, 1991

[51] Int. Cl.⁵ .............. C07K 03/04; C07K 15/20; A61K 37/12
[52] U.S. Cl. ............... 514/21; 530/354; 530/355; 530/410; 530/411; 426/576
[58] Field of Search ......... 530/354, 355, 410, 411; 514/21; 426/576

[56] References Cited

U.S. PATENT DOCUMENTS

| | | | |
|---|---|---|---|
| 2,196,146 | 4/1940 | Collins | 530/354 |
| 3,899,598 | 8/1975 | Fischer et al. | 426/576 |
| 3,904,771 | 9/1975 | Donnelly et al. | 426/576 |
| 4,407,836 | 10/1983 | Bosco et al. | 426/576 |
| 4,500,453 | 2/1985 | Shank | 530/354 |
| 4,615,896 | 10/1986 | Brown et al. | 426/576 |
| 4,670,247 | 6/1987 | Scialpi | 424/484 |

*Primary Examiner*—Merrell C. Cashion, Jr.
*Assistant Examiner*—Andrew G. Rozycki

[57] ABSTRACT

A method for crosslinking protein comprises making an aqueous compositiion of a protein, sugar, a salt, and water, followed by heating the composition while maintaining the moisture content of the composition at a level of at least about 3 weight percent. The composition is made, and the heating carried out, so that the protein is crosslinked to a degree at which it is substantially water insoluble upon being placed in water at 100° C. for at least 3 minutes. A crosslinked protein product comprises a protein crosslinked to a degree that it is substantially water insoluble upon being placed in water at 100° C. for at least 3 minutes, a sugar, a salt, and water.

15 Claims, No Drawings

PROCESS FOR CROSSLINKING GELATIN

BACKGROUND OF THE INVENTION

The present invention relates in general to the field of crosslinking protein, especially gelatin. The crosslinking of protein (and especially gelatin) is a well developed field in which many different means of crosslinking have been proposed.

The process of the present invention requires the use of a protein, a selected sugar (or sugars), a selected salt (or salts), at least a minimal amount of water, and a heating step. Never before the present invention has there been provided any process for crosslinking of protein with these ingredients. This particular combination of ingredients has been unexpectedly found to permit the crosslinking reaction to be performed at temperatures previously inoperable (i.e. too low) to obtain the desired degree of crosslinking with ingredients that are safe for both food and animal feed applications. This "low temperature advantage" is very important because it permits crosslinking to be performed in the presence of the many heat-sensitive materials (which of course have been present during the crosslinking process) without substantial thermal degradation. As a result, heat-sensitive ingredients can now be encapsulated within a gelatin which has been crosslinked, without any substantial degradation of the heat-sensitive ingredient during the crosslinking process. The process of the present invention offers a combination of crosslinking agents which, if making an edible product, are more desirable than previous crosslinking agents and processes in that the crosslinking temperature requirements are lower and/or the crosslinking agents are more desirable for purposes of making edible products.

The present invention is applicable to a wide range of arts, such as food sciences, photographic sciences, pharmaceuticals, etc, i.e. wherever protein crosslinking is utilized in combination with any additional chemical species which may be thermally sensitive, and in all situations in which it is advantageous to conserve energy. The invention is particularly useful in the vitamin arts, especially vitamin A, which undergoes thermal degradation at the temperatures previously required for obtaining substantial protein crosslinking with crosslinking agents which are considered both edible and safe for consumption. Thus the process of the present invention is particularly valuable for crosslinking protein (especially gelatin) in the presence of temperature-sensitive ingredients, such as vitamins, without substantial thermal degradation of the temperature sensitive ingredient.

The advantage is especially important with respect to producing protein-encapsulated vitamin A products. All of the ingredients utilized in the process are both edible and safe for consumption. Thus one is able to use the process of the present invention to obtain a vitamin A encapsulated in a crosslinked gelatin wherein the process is carried out at a temperature at which there is no substantial thermal degradation of the vitamin A.

U.S. Pat. No. 2,196,146 describes subject matter which is related to the present invention. The '146 patent relates to improved food products and process for making the same, and particularly to food products containing sugar and acid, such as those commonly known as gelatin desserts that generally are marketed in the form of a dry powder and usually comprise gelatin. Among the acids mentioned in the '146 patent are "fruit acids" (such as tartaric acid), and to the additional use of salts of organic acids such as acetates. The '146 patent repeatedly refers to the "setting" of the gelatin.

In contrast to the '146 patent, the present invention requires that the protein be "crosslinked". Crosslinking differs from "setting" in that crosslinking is irreversible whereas setting (also known as "gelation") is reversible. The process of setting involves the transformation of a solution to a gel. The addition of heat to the gel can then be used to melt the gel so that a solution is formed. In stark contrast, crosslinking involves an irreversible chemical reaction in that the addition of heat to the crosslinked protein will not result in transforming the crosslinked protein into a solution of the protein.

Another related patent of which applicants are aware is U.S. Pat. No. 4,500,453. This patent relates to crosslinked collagen-derived protein compositions having improved Bloom gel strength and increased viscosity. Furthermore, the '453 patent relates to improvement by crosslinking the protein with an aluminum salt of acetic acid selected from the group consisting of aluminum subacetate, aluminum triacetate and an alkali metal aluminum acetate double salt. The '453 patent requires the use of an aluminum salt, as can be seen from the comparative example therein (Example 2) which states that the substitution of a sodium salt for the aluminum salt is inoperable.

In contrast, the present invention differs from the '453 patent in that the process of the present invention requires the use of at least one of a group of sugars. If one were to alter the process of the present invention by carrying it out in the absence of at least one of these sugars, the required degree of crosslinking will not result. Note Comparative Example 2 herein, which proves that upon using, for example, calcium acetate as the salt, the process of the present invention is inoperable (no crosslinking occurs) in the absence of at least one of the group of sugars. In stark contrast, '453 patent nowhere mentions the use of any sugar, not to mention one or more of the group of sugars which are used in the process of the present invention.

U.S. Pat. No. 4,670,247 refers to a process for the preparation of fat-soluble vitamin active beadlet compositions which exhibit stability when exposed to the feed pelleting process. The process includes forming an aqueous emulsion of a fat-soluble vitamin-active material, gelatin, and a sugar, converting the emulsion to dry particulate form containing the non-aqueous constituents of the emulsion, and heat treating the resulting product to form water insoluble beadlets.

In contrast to the '247 patent, the process of the present invention requires the use of at least one of a group of salts. The '247 nowhere refers to either mandatory use of (or even optional use of) any salt whatsoever. Note Comparative Example 2 herein, which proves that even at a preferred temperature (75° C. for the production of encapsulated vitamin A) for the process of the present invention, inoperability results in the absence of at least one of the group of salts specified.

BRIEF DESCRIPTION OF THE INVENTION

The present invention relates to a process for crosslinking a protein. The protein is crosslinked to a degree that it is substantially insoluble upon being held in boiling water for at least three minutes. The process comprises a first step of making an aqueous composition which comprises:

i. a protein,
ii. a sugar, wherein the sugar is at least one member selected from the group consisting of fructose and glucose,
iii. a salt, wherein the salt is at least one member selected from the group consisting of water-soluble salts of carboxylic acids, sodium carbonate, potassium carbonate, calcium sulfate, and calcium phosphate;
iv. water.

Thereafter, the next step of the process is to heat the composition while maintaining the moisture content of the composition at a level of at least about 3 weight percent. The composition is made, and the heating step performed, so that the protein is crosslinked to a degree at which it is substantially water insoluble upon being placed in water at 100° C. for at least 3 minutes.

It is an object of the present invention to crosslink protein, especially gelatin, using a sugar and a GRAS salt as crosslinking agents.

It is a further object of the present invention to crosslink protein to a degree that the crosslinked protein is substantially insoluble when placed in boiling water (i.e. water boiling at 100° C.) for a period of at least 3 minutes.

It is a further object of the present invention to enable the crosslinking of gelatin at a relatively low temperature (i.e. from about 55° C. to about 85° C.), wherein the crosslinking occurs to a degree that the crosslinked gelatin is substantially insoluble in boiling water for a period of at least 3 minutes.

It is a further object of the present invention to enable the crosslinking of gelatin utilizing a sugar, a GRAS salt, and a moisture level of at least 3 weight percent during the crosslinking reaction.

DETAILED DESCRIPTION OF THE PREFERRED EMBODIMENTS

A primary objective of the process of the present invention is to prepare a substantially crosslinked, water-insoluble protein matrix. A substantially crosslinked, water-insoluble protein matrix is defined as a matrix which is substantially insoluble after 3 minutes in boiling water.

The phrases "crosslinked protein" and "crosslinked gelatin", as commonly used, pertain to a wide spectrum of products having widely differing degrees of crosslinking. The effects of the crosslinking range from a mere increase in the viscosity of the product, to the formation of a very rigid and brittle product which is of course completely insoluble in water. In the field of encapsulating vitamins, pharmaceuticals, food additives, etc, it is desirable to crosslink a protein (especially gelatin) to a degree that the resulting crosslinked matrix is substantially insoluble in boiling water for at least three minutes. If less than this amount of crosslinking is achieved, the encapsulated product will frequently escape during processing, resulting in undesirable degradation, etc of the encapsulated product. It is still more desirable, for certain end uses (such as encapsulated vitamin supplements for use in the manufacture of pelleted animal feeds) that the protein is gelatin and that the gelatin is crosslinked to a degree that it is substantially insoluble upon being placed in water at 100° C. for a period of 15 minutes.

Crosslinking is to be distinguished from gelation in that gelation is the result of hydrogen bonding between individual polymer molecules to form an infinite, 3-dimensional network whereas crosslinking is the result of a chemical reaction between polymer molecules. If polymer molecules are permitted to crosslink to a certain degree, the result is that the crosslinking reaction is irreversible. In contrast, gelation is reversible by merely heating the gel above its melting point.

Heating will generally not reverse a crosslinking reaction. However, reversal of a crosslinking reaction may occur, at least to some degree, if the crosslinking reaction is so slight that the crosslinked bonds between polymer molecules are not strong enough to withstand, for example, thermal stress, such as that from boiling water. For the purposes of encapsulation of vitamins, pharmaceuticals, food additives, flavors, fragrances, photographic additives, etc. in proteins, it is desirable to crosslink the protein to a degree that it is insoluble when placed in boiling water for at least 3 minutes. This level of gelatin crosslinking has surprisingly been found to be achievable with a sugar and a GRAS salt upon heating to relatively low temperatures (e.g. 55° C. to 85° C.) at which certain heat-sensitive ingredients (e.g. vitamin A) are not substantially degraded.

The preferred salt for use in the crosslinking process and product of the present invention is a salt which is categorized as "generally recognized as safe" (i.e. GRAS). GRAS has been defined by the U.S. Food and Drug Administration in parts 182, 184, and 582 of 21 Code of Federal Regulations (21 CFR).

The process of the present invention involves making a composition which comprises a protein, among other ingredients, followed by heating the composition in order to crosslink the protein. The term "composition", as used herein, is meant to require that the combined ingredients are mixed to a degree of substantial uniformity. The composition can be a solution, an emulsion, or a gel.

The composition comprises a protein, a sugar, a salt, and water. Although in general the protein may have a bloom value of from about 0 to about 300, the protein preferably has a bloom value of from about 50 to about 300. It is believed that whereas animal feeds typically utilize gelatin having a bloom value of from about 85 (i.e. from about 80 bloom to about 90 bloom), food additives and pharmaceutical end uses usually utilize gelatin having a bloom value of from about 200 to about 300. Furthermore, the gelatin may be either a Type A or a Type B gelatin. Type A gelatin is obtained from acid processing of collagen. Type B gelatin is obtained from alkaline processing of collagen.

The composition is made by dissolving the protein, the sugar, and the salt in water. In the event that the protein is gelatin, this requires that the gelatin and water be heated to about 60° C. in order to completely dissolve the gelatin.

In general, the protein is present in the composition in an amount of from about 10 weight percent to about 70 weight percent, based on the weight of the composition. Still more preferably the gelatin is present in the composition in an amount of from about 10 weight percent to about 30 weight percent, based on the weight of the composition. Most preferably the protein is present in the composition in an amount of about 17 weight percent, based on the weight of the composition.

Preferably the protein is gelatin. Preferably the gelatin has a bloom of from about 50 to about 300. Most preferably the gelatin has a bloom value of about 85 if the product of the process is to be utilized as a vitamin supplement for animal feed.

The composition further comprises a sugar. As with the protein, the sugar is also dissolved in water in making the composition. In general, the sugar is at least one member selected from the group consisting of fructose and glucose. The term fructose is meant to include not simply pure fructose, but also high fructose corn syrup, isomers of fructose, as well as fructose-bearing mixtures such as invert sugar (a mixture of fructose and glucose). The term glucose is meant to include not simply pure glucose, but also isomers of glucose, such as mannose, as well as glucose-bearing mixtures such as high glucose corn syrup. Most preferably the sugar is high fructose corn syrup.

In general, the sugar is present in the composition in an amount of from about 3 weight percent to about 30 weight percent, based on the weight of the composition. Preferably the sugar is present in the composition in an amount of from about 5 weight percent to about 20 weight percent, based on the weight of the composition. Most preferably the sugar is present in an amount of about 10 weight percent, based on the weight of the composition.

The composition further comprises a salt, wherein the salt is at least one member selected from the group consisting of water-soluble salts of carboxylic acids, sodium carbonate, potassium carbonate, calcium sulfate, and calcium phosphate. Upon making the composition, the salt is completely dissolved in water. Preferably, the water-soluble salt is at least one member selected from the group consisting of sodium acetate, calcium acetate, sodium propionate, calcium propionate, sodium benzoate, sodium carbonate, potassium carbonate, calcium sulfate, calcium phosphate, sodium tartrate, and sodium glutarate. More preferably the salt is at least one member selected from the group consisting of sodium acetate, calcium acetate, sodium propionate, calcium propionate, sodium benzoate, sodium carbonate, and potassium carbonate. Most preferably the salt is sodium acetate.

In general, the water soluble salt of the carboxylic acid is present in the composition in an amount of from about 0.5 weight percent to about 25 weight percent, based on the weight of the composition. Preferably the salt is present in the composition in an amount of from about 1 weight percent to about 10 weight percent, based on the weight of the composition. Most preferably the salt is present in the composition in an amount of about 2 weight percent, based upon the weight of the composition.

The composition further comprises water. The water content of the composition is considerably greater before the heating step than after the heating step, because the initial water content of the composition must be high enough to dissolve the protein (gelatin), sugar, salt, and possibly even an additional ingredient(s), if it is water soluble. However, once the ingredients are dissolved, the composition is most preferably allowed to gel, and thereafter the gel is preferably dried to a moisture content of from about 15 weight percent to about 3 weight percent, before the heating step is initiated.

Upon first making the composition, the water is present in an amount which is great enough to at least dissolve all of the protein (gelatin), sugar, and salt present in the composition. In general, the water (i.e. moisture) content of the composition is from about 3 weight percent to about 90 weight percent, based on the weight of the composition. Preferably the moisture content of the composition is from about 25 weight percent to about 60 weight percent, based on the weight of the composition. Most preferably the moisture content of the composition is about 48 weight percent.

After the gelatin, sugar, and salt are dissolved, during the heating step the moisture content may be reduced to a level down to as low as about 3 weight percent, based on the total (reduced) weight of the composition. It has been found that the crosslinking reaction can be carried out at relatively low temperatures (i.e. from about 55° C. to about 85° C.) so long as the moisture content of the composition being heated is at least about 3 weight percent. Most preferably the moisture content of the composition is about 7 weight percent during the heating step.

The composition may (but need not) further comprise an additional ingredient. Examples of additional ingredients which may be used in the present invention include: vitamins, pharmaceuticals, flavors, fragrances, food additives, photographic additives, etc. There are thousands of possible additional ingredients for use in the present invention. The additional ingredient may be either encapsulated within the crosslinked protein matrix, or may be simply entrapped within the crosslinked protein matrix. If the additional ingredient is insoluble in the aqueous composition, and an emulsion is formed before the heating step, the result will be an additional ingredient which is encapsulated within the crosslinked protein matrix. If the additional ingredient is soluble in the aqueous composition, the result will be an additional ingredient which is entrapped within the crosslinked protein matrix.

Preferred additional ingredients are vitamins. Still more preferred additional ingredients are fat-soluble vitamins, which are of course not substantially water soluble. The fat-soluble vitamins, when combined with the aqueous composition, are preferably thereafter agitated so that an emulsion is formed.

A most preferred additional ingredient is vitamin A oil. Since vitamin A oil is substantially insoluble in the aqueous composition, emulsification of the vitamin A oil can be used to produce an encapsulated vitamin A product in which a crosslinked gelatin matrix is insoluble when placed in boiling water for at least three minutes. This is a very desirable result since the encapsulated vitamin A product can be utilized in feed formulations which are subjected to the harsh conditions (high temperature, high pressure, and high shear) found in pelleting and extrusion operations. Just as importantly, the present invention enables this relatively high degree of crosslinking without subjecting the vitamin A oil to a temperature at which degradation of the vitamin occurs. Vitamin A oil is particularly sensitive to being heated in the presence of oxygen, the vitamin A degrading when heated in the presence of oxygen at temperatures of 90° C. Even minimal degradation of the vitamin A oil (e.g. 2% degradation) results in significant loss of value, since the cost of the vitamin A oil is so much greater than the cost of the other ingredients (i.e. the gelatin, sugar, and salt) utilized in the formulation.

In general, the additional ingredient may be present in the composition in an amount of from about 0.1 weight percent to about 60 weight percent, based on the weight of the composition before the heating or drying step. Preferably the additional ingredient is present in an amount of from about 5 weight percent to about 55 weight percent. Most preferably the additional ingredient is present in an amount of from about 22 weight percent.

The process of the present invention need not require an additional ingredient. That is, there are certain uses for crosslinked protein (gelatin) which do not require that the crosslinked protein contain any additional ingredient. Such uses are crosslinked gelatin foams, crosslinked gelatin films, pharmaceutical capsules, and glues.

Once the composition is made by combining the protein, sugar, salt, water, and additional ingredient, the composition is then heated in order to crosslink the protein. The heating step is carried out in order to crosslink the protein to a degree at which it is substantially water insoluble upon being placed in boiling water (i.e. at 100° C.) for at least 3 minutes. Still more preferably, the composition is made, and the heating step carried out, so that the protein is crosslinked to a degree at which it is substantially water insoluble upon being placed in boiling water (i.e. at 100° C.) for at least 15 minutes.

Throughout that period of the heating step during which the crosslinking reaction is taking place, it has been found necessary to keep the moisture content of the composition at a level of at least about 3 weight percent, based on the total weight of the composition. In general, during the heating step the moisture content of the composition may be within the range of from about 3 weight percent up to about 90 weight percent. However, it has been found that the maximum amount of water which can be present during the crosslinking reaction varies depending upon the particular salt utilized. It has been found that if sodium carbonate is utilized as the salt, the water content may be at least as high as 60 weight percent, based on the total weight of the composition (see Example 11, infra). However, if the salt utilized is sodium acetate, the maximum amount of water which can be present during the crosslinking reaction is about 30 weight percent water. For most of the salts which can be used in the present invention, the maximum amount of moisture at which the crosslinking reaction will occur is about 30 weight percent.

In general, the heating may be carried out at any temperature desired and for any period of time desired, so long as the protein is crosslinked to a degree that it is insoluble in boiling water for at least three minutes. If gelatin is the protein utilized in the composition, the temperature range to be utilized may be from about 50° C. to about 180° C. However, if a heat-sensitive additional ingredient is present during the crosslinking step (i.e. an ingredient such as vitamin A, which begins to degrade at a substantial rate at temperatures around 90° C.), it is preferable to carry out the heating step within a temperature range of from about 55° C. to about 85° C. Most preferably the heating step is carried out at a temperature of about 75° C.

The duration of the heating step is quite broad, depending upon the temperature employed in the process. If a relatively high temperature is employed (e.g. around 180° C.), the heating step need be no longer than about 30 seconds to a few minutes in order to produce the desired degree of crosslinking. If a relatively low temperature is employed (e.g. from about 55° C. to about 80° C.), the heating step may be carried out for a period of several hours (e.g. from at least 2 hours to about 24 hours) in order to produce the desired degree of crosslinking.

A moisture content of at least 3 weight percent has been found to be necessary in order to sustain the crosslinking reaction. Thus, it is necessary to maintain this moisture level during that portion of the heating step that the crosslinking reaction is to progress. Further heating after the moisture content has dropped below 3 weight percent will not sustain further crosslinking of the protein, and is also undesirable if a heat-sensitive ingredient is present in the composition. As a general rule, the heating step should be carried out at a temperature below that at which any heat-sensitive ingredient degrades, and as a general rule the heating step should be no longer than that period required to produce the desired degree of crosslinking.

The present invention also relates to a crosslinked protein product which encapsulates (or entraps) an additional ingredient. In general, the product of the present invention comprises:

A. a protein which is crosslinked to a degree at which it is substantially insoluble upon being placed in boiling water for at least 3 minutes;
B. a sugar wherein the sugar is at least one member selected from the group consisting of fructose and glucose;
C. a salt wherein the salt is at least one member selected from the group consisting of water-soluble salts of carboxylic acids, sodium carbonate, potassium carbonate, calcium sulfate, and calcium phosphate; and
D. water.

The crosslinked protein in the product of the present invention is a protein as may be produced by the above-described process of the present invention. The protein is preferably gelatin, and may be a gelatin having a bloom of from about 50 to about 300. The gelatin most preferably has a bloom of about 85 (i.e. a bloom of rom about 80 to about 90). The protein is crosslinked to a degree at which it is substantially insoluble upon being placed in boiling water for at least 3 minutes. Still more preferably the protein is crosslinked to a degree at which it is substantially insoluble upon being placed in boiling water for at least 15 minutes.

In general, the crosslinked protein is present in the product in an amount of from about 10 weight percent to about 70 weight percent, based on the weight of the product. Preferably the crosslinked protein is present in an amount of from about 15 weight percent to about 50 weight percent, based on the weight of the product. Most preferably the protein is present in an amount of about 30 weight percent, based on the weight of the product.

The sugar in the product of the present invention is a sugar as is described above with reference to the process of the present invention. Generally, the sugar of the present invention is at least one member selected from the group consisting of fructose and glucose. These terms are again used as is described above with reference to the process of the present invention. Most preferably the sugar is high fructose corn syrup.

In general, the sugar is present in the product in an amount of from about 3 weight percent to about 30 weight percent, based on the weight of the product. Preferably the sugar is present in the product in an amount of from about 10 weight percent to about 30 weight percent, based on the weight of the product. Most preferably the sugar is present in an amount of about 20 weight percent, based on the weight of the product.

The product further comprises a salt wherein the salt is at least one member selected from the group consisting of water-soluble salts of carboxylic acids, sodium carbonate, potassium carbonate, calcium sulfate, and calcium phosphate. More specifically, the water-soluble salt is at least one member selected from the group consisting of sodium acetate, calcium acetate, sodium propionate, calcium propionate, sodium benzoate, sodium carbonate, potassium carbonate, calcium sulfate, calcium phosphate, aluminum subacetate, sodium tartrate, and sodium glutarate. Preferably the salt is at least one member selected from the group consisting of sodium acetate, calcium acetate, sodium propionate, calcium propionate, sodium benzoate, sodium carbonate, and potassium carbonate. Most preferably the salt is sodium acetate.

In general, the water-soluble salt of the carboxylic acid is present in the product in an amount of from about 0.5 weight percent to about 25 weight percent, based on the weight of the product. Preferably the salt is present in the product in an amount of from about 2 weight percent to about 10 weight percent, based on the weight of the product. Most preferably the salt is present in the product in an amount of about 5 weight percent, based upon the weight of the product.

The product further comprises water. In general, water is present in the product in an amount of from about 1 weight percent to about 18 weight percent, based on the weight of the product. Preferably water is present in an amount of from about 3 weight percent to about 13 weight percent, and most preferably water is present in an amount of about 4 weight percent, based on the weight of the product. If a vitamin emulsion containing gelatin is spray congealed, and then crosslinked to the degree specified herein, it is most preferred that the product is dried to a moisture content of about 4 weight percent, based on the weight of the product.

The product may optionally further comprise an additional ingredient. Examples of additional ingredients which may be used in the present invention include: vitamins, pharmaceuticals, flavors, fragrances, food additives, photographic additives, etc. There are thousands of possible additional ingredients for use in the present invention. The additional ingredient may be either encapsulated within the crosslinked protein matrix, or may be simply entraped within the crosslinked protein matrix. If the additional ingredient is insoluble in water, the product will comprise an additional ingredient which is encapsulated within the crosslinked protein matrix. If the additional ingredient is soluble in the aqueous composition, the product will comprise an additional ingredient which is entrapped within the crosslinked protein matrix.

The additional ingredient may be a water-soluble vitamin. The water-soluble vitamin will be entrapped within the crosslinked protein matrix. The water-soluble vitamin may be at least one member selected from the group consisting of vitamin C, thiamine, pyridoxine, riboflavin, biotin, nicotinamide, folic acid, cobalamin, and pantothenic acid.

More preferably the additional ingredient is a fat-soluble vitamin which is at least one member selected from the group consisting of vitamin A, carotinoids, vitamin D, vitamin E, and vitamin K. The fat-soluble vitamin is encapsulated within the crosslinked protein (preferably gelatin) matrix. The most preferred additional ingredient is vitamin A oil.

The additional ingredient may comprise both fat-soluble as well as water-soluble vitaims.

In general, the additional ingredient may be present in the product in an amount of from about 0.1 weight percent to about 60 weight percent, based on the weight of the product. Preferably the additional ingredient is present in an amount of from about 10 weight percent to about 50 weight percent. Most preferably the additional ingredient is present in an amount of about 40 weight percent.

EXAMPLES

Example 1: Preparation of Gelatin Slabs

The gelatin compositions described in the examples below were prepared b dissolving gelatin and other ingredients in water at 60° C., then allowing the resulting solutions to set, or gel, at ambient temperature, into slabs approximately 1 to 2 millimeters in thickness and approximately 75 millimeters in diameter. The gelled slabs were then allowed to dry at ambient temperature and humidity for about 16–20 hours, with a final moisture content of about 25 weight percent (based on the weight of the slab).

Example 2

Three solutions (solutions A, B and C) were prepared. Each solution contained 18.6 parts by weight Type B gelatin having a bloom value of from about 80 to about 90 dissolved in 50.2 parts (by weight) water heated at 60° C. to dissolve the gelatin. Additionally, solution A contained fructose (3 parts), solution B contained calcium acetate (3 parts), and solution C contained calcium acetate (3 parts) and fructose (3 parts).

Two slabs were prepared from each solution, via the procedure described in Example 1, supra. One slab from each solution was placed in an oven at 70° C. for 6 hours, then cooled to ambient temperature. The other slabs were not heated, these slabs being used as controls. Upon completion of the heating, all six slabs were then placed in boiling water with stirring. The control slabs for solutions A, B and C, as well as the heat-treated slabs for solutions A and B underwent substantially complete dissolution in less than 3 minutes, indicating an absence of any substantial amount of crosslinking. The heat-treated slab from solution C remained substantially insoluble after 10 minutes, indicating a substantial degree of crosslinking.

This example shows the need for both sugar and salt in order to effectuate substantial crosslinking.

Example 3

High fructose corn syrup (13.4 parts) and sodium acetate (2.1 parts) were dissolved in water (43 parts). Gelatin (19.2 parts, 80-90 Bloom, Type B) was added, and the solution was heated to 60° C. to dissolve the gelatin. Vitamin A acetate oil (22.3 parts of oil having 2.1 million international units {MIU} per gram) containing ethoxyquin (80 mg/MIU vitamin·A) and BHT (10 mg/MIU vitamin A) was added and the resulting mixture was homogenized at 60° C., resulting in an aqueous emulsion with oil droplets approximately 2 microns in diameter.

The emulsion was then spray-congealed using hydrophobic starch as the absorbant. The vitamin-active beadlets were then separated from the excess starch so that a product was obtained in which the beadlets ranged in size between about 105 microns to about 840 microns. The resulting beadlets were dried in a fluid-bed dryer to a moisture of about 6.0 weight percent. The beadlets were then heated to 75° C. for eight hours in the fluid-bed dryer with humidified air so that the moisture of the beadlets was maintained between 6 and 9 weight percent. When the heating was complete, the beadlets were dried to a final moisture content of 4.1%. The final product was substantially crosslinked, being substantially insoluble in boiling water for greater than 15 minutes.

Example 4

Three gelatin solutions were prepared by dissolving gelatin (18.6 parts, 80-90 Bloom Type B), fructose (5.3 parts) and calcium acetate (5.0 parts) in water (50.2 parts) heated at 60° C. Calcium hydroxide was added to each solution (0.15, 0.30 and 0.45 parts, respectively) to adjust the pH (at 60° C.) of the solutions to 7.0, 8.0 and 9.0, respectively.

A slab was prepared for each solution as described in Example 1 (supra). The slabs were then heated at 70° C. for 6 hours. During heating, all three slabs turned color from straw-colored to dark brown. The slabs were then placed in boiling water with stirring. All three slabs were substantially insoluble after 12 minutes, indicating each slab was substantially crosslinked. However, the gelatin matrix integrity appeared to increase with increasing pH.

This example illustrates the effect of pH on the process for producing a crosslinked gelatin matrix.

Example 5

Fructose (3.0 parts), sodium acetate (5.0 parts) and hydrolyzed gelatin (18.6 parts) were dissolved in water (50.2 parts) heated at 60° C. Two slabs were prepared as described in Example 1, supra. One slab was placed in an oven at 70° C. for 6 hours, then cooled to ambient temperature, the other slab was kept as a control. The heated slab turned from straw-colored to dark brown during heating. Both slabs were then placed in boiling water with stirring. The control slab underwent substantially complete dissolution in less than 1 minute, while the heat-treated slab took longer (less than 3 minutes) to completely dissolve.

These results indicate that hydrolyzed gelatin can be crosslinked by the process of the present invention, but not to the same degree as unhydrolyzed gelatin.

Example 6

Fructose (5.2 parts), calcium acetate (4.3 parts), glycerin (2.2 parts) and caramel color (2.4 parts) were dissolved in water (50.3 parts). Gelatin (22.9 parts, 80-90 Bloom Type B) was added and the solution was heated to 60° C. to dissolve the gelatin. Vitamin A acetate oil (24.3 parts of 2.1 MIU/g) containing ethoxyquin (80 mg/MIU vitamin A) and BHT (10 mg/MIU vitamin A) was added, and the resulting mixture was homogenized at 60° C., resulting in an aqueous emulsion with oil droplets approximately 2 microns in diameter.

The emulsion was then spray-congealed using hydrophobic starch as the absorbant. The vitamin-active beadlets were then separated from the excess starch so that a product was obtained in which the beadlets ranged in size between about 105 microns to about 840 microns. The resulting product was dried in a fluid-bed dryer to a moisture of about 8.0 weight percent. The product was then heated in the fluid-bed to 75° C. for 8 hours with hot, humidified air, so that the moisture content of the product was maintained between 6 and 9 weight percent during the course of heating. When the heating was complete, the product was dried to a final moisture content of 4.1%. The final product was substantially crosslinked, being substantially insoluble in boiling water for greater than 15 minutes.

Example 7

Three solutions, A, B, and C, were prepared, each containing gelatin (18.6 parts, 80-90 Bloom, Type B) dissolved in water (50.2 parts) heated at 60° C. Additionally, solution A contained sodium acetate (5 parts) and sucrose (3 parts), solution B contained calcium acetate (5 parts) and sucrose (3 parts), and solution C contained sucrose (3 parts), but no salt. Slabs were prepared for each solution as described in Example 1 (supra), then heated at 70° C. for 6 hours. No color change was observed during heating for any of the slabs. After cooling to ambient temperature, the slabs were placed in boiling water with stirring. All three slabs underwent substantially complete dissolution in less than 2 minutes, indicating that no substantial crosslinking occurred during heating of any of the slabs.

Example 8

Five solutions were prepared containing sodium acetate (5 parts), gelatin (18.6 parts, 80-90 Bloom, Type B) and water (50.2 parts). Each solution was heated to 60° C. in order to dissolve the gelatin. In addition, each solution contained one of the following sugars: glucose (5.6 parts), mannose (5.6 parts), invert sugar (5.6 parts), corn syrup (4 parts, containing approximately 75 weight percent solids) and high fructose corn syrup (5.6 parts). Slabs were prepared for each solution as described in Example 1 (supra). The five slabs were then heated at 70° C. for 6 hours. The glucose, mannose, invert sugar and high fructose corn syrup slabs all turned dark brown during heating. The corn syrup slab turned amber during heating.

After heating, the slabs were allowed to cool to ambient temperature. The cooled slabs were then placed in boiling water, with stirring. All 5 slabs remained substantially insoluble after at least 5 minutes in boiling water, indicating they were all substantially crosslinked.

Example 9

Three solutions, A, B and C, were prepared by dissolving gelatin (11.4 parts, 80-90 Bloom, Type A) in 88.6 parts water heated to 45°-50° C. Additionally, solutions A and B both contained aluminum subacetate filtrate (ASF) solution (6.58 parts stock solution diluted with 13.16 parts water, prepared fresh as described by Shank in U.S. Pat. No. 4,500,453, column 8, lines 1-67) which was added slowly with vigorous stirring, being careful to maintain the temperature of the gelatin solutions above 35° C. Solution B also contained fructose (2.7 parts). In addition to gelatin and water, solution C also contained undiluted ASF stock solution (18 parts) and fructose (2.7 parts).

Once addition of the ASF solution was complete, two slabs were prepared for each solution as described in Example I, supra. Then, one slab for each solution was heated at 70° C. for 6 hours, while the other slab was kept as a control. All 3 control slabs were clear and colorless.

After heating, the appearance of slab A remained unchanged, but slabs B and C had darkened. All 6 slabs were then placed in boiling water with stirring. The 3 control slabs underwent substantially complete dissolution in less than 2 minutes. Heat-treated slabs A and B underwent substantially complete dissolution in less than 3 minutes. Heat-treated slab C completely dissolved in less than 4 minutes.

Example 10

Four solutions (A, B, C and D) were prepared, each containing gelatin (18.6 parts, 80-90 Bloom, Type B) and fructose (3 parts) dissolved in water (50.2 parts) which was heated to 60° C. Additionally, solution A contained sodium propionate (3 parts) and glycerin (2.3 parts), solution B contained calcium propionate (3 parts) and glycerin (2.3 parts), solution C contained sodium benzoate (5.0 parts) and solution D contained potassium carbonate (5.0 parts). Slabs were prepared for each solution as described in Example 1, supra and heated at 70° C. for 6 hours. All four slabs turned dark brown during heating The slabs were then placed into boiling water with stirring. All four slabs remained substantially insoluble after 15 minutes in boiling water, indicating each slab underwent a substantial degree of crosslinking.

Example 11

Gelatin (18.6 parts, 80-90 Bloom Type B), fructose (3.0 parts) and sodium carbonate (5.0 parts) were dissolved in water (50.2 parts) heated at 60° C. Once the gelatin had dissolved, the temperature of the solution was increased to about 75° C., at which point a strong amine odor developed, followed by a rapid increase in viscosity. Within 10 minutes at about 75° C. the solution had set into a gel which was dark amber in color and insoluble in water.

This Example illustrates that the process of the present invention can be carried out using water in an amount of about 60 weight percent, based on the weight of the composition. However, further experiments have revealed that the process can be carried out using water in an amount of about 80 weight percent. Therefore, it is believed that the process can be carried out with a composition comprising water in an amount of as high as about 90 weight percent, based on the weight of the composition.

We claim:

1. A method for crosslinking gelatin, comprising the steps of:
   A. making an aqueous composition of:
      i. a gelatin,
      ii. a sugar, wherein the sugar is at least one member selected from the group consisting of fructose and glucose,
      iii. a salt, wherein the salt is at least one member selected from the group consisting of water-soluble salts of carboxylic acids, sodium carbonate, potassium carbonate, calcium sulfate, and calcium phosphate;
      iv. water; and
   B. heating the composition at a temperature of from about 55 degrees C. to about 85 degrees C. while maintaining the moisture content of the composition at a level of at least about 3 weight percent,
   so that the gelatin is crosslinked to a degree at which it is substantially water insoluble upon being placed in water at 100° C. for at least 3 minutes.

2. The method of claim 1 wherein the salt is at least one member selected from the group consisting of sodium acetate, calcium acetate, sodium propionate, calcium propionate, sodium benzoate, sodium carbonate, potassium carbonate, calcium sulfate, calcium phosphate, sodium tartrate, sodium glutarate, and aluminum subacetate.

3. The method of claim 2 wherein the composition comprises the gelatin in an amount of from about 10 weight percent to about 70 weight percent, the sugar in an amount of from about 3 to about 30 weight percent, the salt in an amount of from about 0.5 to about 25 weight percent, and water in an amount of from about 3 to about 90 weight percent.

4. The method of claim 3 wherein the gelatin has a bloom of from about 50 to about 300.

5. The method of claim 3 wherein the heating is carried out for a period of at least 30 seconds.

6. The method of claim 2, wherein the composition comprises gelatin in an amount of from about 10 weight percent to about 30 weight percent, the sugar in an amount of from about 5 to about 20 weight percent, the salt in an amount of from about 1 to about 10 weight percent, and water in an amount of from about 3 to about 60 weight percent.

7. A method for crosslinking gelatin, comprising the steps of:
   A. making an aqueous solution comprising:
      i. a gelatin having a bloom of from about 50 to about 300, the gelatin being present in the composition in an amount of from about 10 weight percent to about 70 weight percent, based on the weight of the solution,
      ii. a sugar, wherein the sugar is at least one member selected from the group consisting of fructose and glucose, the sugar being present in the composition in an amount of from about 3 weight percent to about 50 weight percent, based on the weight of the solution;
      iii. a salt, wherein the salt is at least one member selected from the group consisting of sodium acetate, calcium acetate, sodium propionate, calcium propionate, sodium benzoate, sodium carbonate, potassium carbonate, calcium sulfate, calcium phosphate, wherein the salt is present in an amount of from about 0.5 weight percent to about 25 weight percent, based upon the weight of the composition;
      iv. water, in an amount of from about 25 weight percent to about 90 weight percent, based on the weight of the composition; and
   B. gelling the aqueous solution;
   C. reducing the moisture content of the gel to a reduced level of from about 15 weight percent to about 4 weight percent, based on the weight of the composition;
   D. heating the gel to a temperature of from about 55° C. to 85° C. for a period of from at least 2 hours to about 24 hours, while substantially maintaining the moisture content of the gel at the reduced moisture level,
   so that the gelatin is crosslinked to a degree at which it is substantially water insoluble upon being placed in water at 100° C. for at least 3 minutes.

8. The method of claim 7, wherein the composition comprises gelatin in an amount of from about 10 weight percent to about 30 weight percent, the sugar in an amount of from about 5 to about 20 weight percent, the salt in an amount of from about 1 to about 10 weight percent, and water in an amount of from about 3 to about 60 weight percent, and wherein the method is carried out so that the gelatin is crosslinked to a degree that it is substantially insoluble upon being placed in water at 100° C. for at least 15 minutes.

9. A crosslinked gelatin product, comprising:

A. a gelatin wherein the gelatin is crosslinked to a degree at which it is substantially water insoluble upon being placed in water at 100° C. for at least 3 minutes.
B. a sugar, wherein the sugar is at least one member selected from the group consisting of fructose and glucose;
C. a salt which is at least one member selected from the group consisting of water-soluble salts of carboxylic acids, sodium carbonate, potassium carbonate, calcium sulfate, and calcium phosphate; and
D. water.

10. The crosslinked gelatin product of claim 9, wherein the salt is at least one member selected from the group consisting of sodium acetate, calcium acetate, sodium propionate, calcium propionate, sodium benzoate, sodium carbonate, potassium carbonate, calcium sulfate, calcium phosphate, sodium tartrate, and sodium glutarate.

11. The product of claim 10 wherein the gelatin is present in an amount of from about 10 weight percent to about 70 weight percent, based on the weight of the product, the sugar is present in an amount of from about 3 to about 30 weight percent, based on the weight of the product, the salt is present in an amount of from about 0.5 to about 25 weight percent, based on the weight of the product, the water is present in an amount of from about 1 weight percent to about 18 weight percent, based on the weight of the product.

12. The product of claim 11 wherein the gelatin has a bloom of from about 50 to about 300.

13. The product of claim 11, wherein:
A. the gelatin has a bloom of from about 50 to about 300, the gelatin being present in an amount of from about 15 weight percent to about 50 weight percent, based upon the weight of the product,
B. the sugar is at least one member selected from the group consisting of fructose and glucose, wherein the sugar is present in an amount of from about 10 weight percent to about 30 weight percent, based upon the weight of the product;
C. the salt is at least one member selected from the group consisting of sodium acetate, calcium acetate, sodium propionate, calcium propionate, sodium benzoate, sodium carbonate, potassium carbonate, calcium sulfate, and calcium phosphate, wherein the salt is present in an amount of from about 2 weight percent to about 10 weight percent, based upon the weight of the product;
D. the water is present in an amount of from about 3 weight percent to about 13 weight percent.

14. The product of claim 13, wherein the gelatin has a bloom of from about 80 to about 90, the sugar is high fructose corn syrup, and the salt is sodium acetate.

15. The product of claim 14 wherein the gelatin is crosslinked to a degree that it is substantially water insoluble upon being placed in water at 100° C. for a period of 15 minutes.

* * * * *